United States Patent
Anekal et al.

(10) Patent No.: US 10,730,021 B2
(45) Date of Patent: *Aug. 4, 2020

(54) SYSTEMS, DEVICES, AND METHODS FOR BODILY FLUID SEPARATION MATERIALS

(71) Applicant: Theranos IP Company, LLC, Healdsburg, CA (US)

(72) Inventors: Samartha Anekal, San Jose, CA (US); Deborah Sloan, San Ramon, CA (US)

(73) Assignee: Labrador Diagnostics LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/424,873

(22) Filed: May 29, 2019

(65) Prior Publication Data
US 2020/0023318 A1    Jan. 23, 2020

Related U.S. Application Data

(63) Continuation of application No. 15/714,648, filed on Sep. 25, 2017, now Pat. No. 10,328,395, which is a continuation of application No. 14/214,772, filed on Mar. 15, 2014, now Pat. No. 9,795,929.

(60) Provisional application No. 61/799,221, filed on Mar. 15, 2013.

(51) Int. Cl.
| | |
|---|---|
| *B01D 69/12* | (2006.01) |
| *B01D 69/06* | (2006.01) |
| *B01D 71/68* | (2006.01) |
| *A61M 1/34* | (2006.01) |
| *B01D 65/02* | (2006.01) |
| *B01D 67/00* | (2006.01) |

(52) U.S. Cl.
CPC ............ *B01D 69/12* (2013.01); *A61M 1/34* (2013.01); *A61M 1/3403* (2014.02); *B01D 65/02* (2013.01); *B01D 67/0088* (2013.01); *B01D 69/06* (2013.01); *B01D 71/68* (2013.01); *A61M 2202/0415* (2013.01); *A61M 2207/00* (2013.01); *B01D 2325/14* (2013.01); *B01D 2325/16* (2013.01)

(58) Field of Classification Search
CPC ........... B01D 2325/14; B01D 2325/16; B01D 65/02; B01D 67/0088; B01D 69/06; B01D 69/12; B01D 71/68; A61M 1/34; A61M 1/3403; A61M 2207/00; A61M 2202/0415
See application file for complete search history.

(56) References Cited

U.S. PATENT DOCUMENTS

| | | |
|---|---|---|
| 5,151,129 A | 9/1992 | Morrison et al. |
| 5,447,417 A | 9/1995 | Kuhl et al. |
| 5,578,269 A | 11/1996 | Yaremko et al. |
| (Continued) | | |

OTHER PUBLICATIONS

Office Action dated Nov. 28, 2016 for U.S. Appl. No. 14/214,772.
(Continued)

*Primary Examiner* — John Kim

(57) ABSTRACT

In one embodiment described herein, a bodily fluid separation material is provided comprising a formed component capture region and a bodily fluid pass-through region. The pass-through region has structures with a reduced liquid leaching quality relative to than the capture region, wherein during separation material use, bodily fluid enters the capture region prior to entering the pass-through region. Optionally, a bodily fluid pass-through region has a reduced amount of liquid leaching material relative to than the capture region.

15 Claims, 3 Drawing Sheets

(56) References Cited

U.S. PATENT DOCUMENTS

| | | |
|---|---|---|
| 9,795,929 B2 | 10/2017 | Anekal et al. |
| 2006/0228258 A1 | 10/2006 | Samsoondar |
| 2009/0162941 A1 | 6/2009 | Winkler et al. |
| 2009/0240165 A1 | 9/2009 | Yoneya et al. |
| 2009/0306543 A1 | 12/2009 | Slowey et al. |
| 2010/0012577 A1 | 1/2010 | Krause et al. |
| 2010/0184056 A1 | 7/2010 | Weinberger et al. |
| 2010/0320146 A1 | 12/2010 | Krause et al. |
| 2011/0124025 A1 | 5/2011 | Castracane et al. |
| 2011/0312481 A1 | 12/2011 | Nguyen et al. |
| 2012/0275955 A1 | 11/2012 | Haghgooie et al. |
| 2013/0172780 A1 | 7/2013 | Kuenstner |
| 2014/0219886 A1 | 8/2014 | Choi et al. |
| 2018/0104656 A1 | 4/2018 | Anekal et al. |

OTHER PUBLICATIONS

Office Action dated Dec. 29, 2016 for U.S. Appl. No. 14/446,080.
Office Action dated Mar. 16, 2016 for U.S. Appl. No. 14/214,772.
Office Action dated Apr. 6, 2018 for U.S. Appl. No. 15/714,648.
Office Action dated Aug. 24, 2018 for U.S. Appl. No. 15/714,648.

SYSTEMS, DEVICES, AND METHODS FOR BODILY FLUID SEPARATION MATERIALS

COPYRIGHT

This document contains material subject to copyright protection. The copyright owner (Applicant herein) has no objection to facsimile reproduction of the patent documents and disclosures, as they appear in the US Patent and Trademark Office patent file or records, but otherwise reserves all copyright rights whatsoever. The following notice shall apply: Copyright 2013 Theranos, Inc.

BACKGROUND

Certain separation materials can be used for separating plasma from whole blood. One example of such a separation material is an asymmetric separation membrane, which can be used to separate solid or semi-solid components from liquid components through the principle of size exclusion. For plasma separation, the asymmetric separation membrane traps formed blood components such as red and white blood cells in the larger pores at the top of the separation material and allows plasma to filter through the smaller pores at the bottom of the separation material.

The filtered plasma can then be used for other purposes such as but not limited to analyte measurement. For assay uses, plasma separation membranes have been used commercially for large molecule assays for certain proteins and lipids. Examples include assays directed at cardiac biomarkers such as Troponin I, albumin, cholesterol, etc. Most of the current applications of plasma separation membranes are in lateral flow assays, where the separation material is mounted on top of another absorbent material which houses the assay reagents and where the reaction happens. This limits the use of this separation membrane to a limited set of assays which use mostly undiluted plasma and which can be performed on a surface.

Unfortunately, these conventional plasma separation membranes are configured in manner that can negatively interfere with plasma sample integrity, particularly when the plasma is used for certain assays. For example, a hemolysis preventing agent typically used with such separation membranes is a substance that can leach out of the separation membrane surface and into the collected plasma sample, which can then result in erroneous measurements for certain assays. Although the anti-hemolytic effect is generally desirable for sample integrity, errors associated with such coatings is not desirable.

SUMMARY

At least some disadvantages associated with the prior art are overcome by at least some or all of the embodiments described in this disclosure. Although the embodiments herein are typically described in the context of obtaining a blood sample, it should be understood that the embodiments herein are not limited to blood samples and can also be adapted for use with other fluid(s) or bodily sample(s).

In one embodiment described herein, it is desirable to use separation materials on a bodily fluid to allow for plasma-based assays. The desired list of assays includes not only large molecules such as proteins and lipids, but also smaller metabolites such as those that are part of the complete metabolic panel and examples include but are not limited to glucose, calcium, magnesium, etc. . . . . Since the plasma separation materials were not primarily designed for these assays but for use in select types of test-strip based assays, the hemolysis-preventing agent used in these materials can interfere with other assay chemistries.

In the case of at least some bodily fluid separation materials described herein, the separation material may have a coating of a protective material such as but not limited to an anti-hemolytic material like single and/or double alkyl chain N-oxides of tertiary amines (NTA). Alternatively, separation material coating can constitute a combination of an anti-hemolytic (such as surfactant, protein, sugar, or a combination of these), alongside an anti-coagulant (such as EDTA and its derivatives or Heparin). NTA generally does not interfere with several large molecule assays. NTA, however, is a chelating agent that strongly binds to di-valent cations such as calcium and magnesium ions. Unfortunately, this results in a very strong interference in certain assays used to measure, for example and not limitation, calcium and magnesium concentrations and also for assays where Ca and Mg are co-factors for enzymes which are part of the reaction. This can result in significant errors for such assays.

One or more of the embodiments described herein provide the benefits of the anti-hemolytic material but also provide a much reduced downside effect of the anti-hemolytic material leaching into the bodily fluid and altering the assay results. It should be understood that the coating, in some embodiments, can be one or more of the following: anti-coagulant, anti-hemolytic, and molecules for surface coverage. Any of these may interfere with assays. Some embodiments disclosed herein are directed toward multi-region separation material structures with capture region(s) and pass-through region(s) with different surface treatments.

Optionally, these separation materials may be asymmetric or non-asymmetric separation materials. Some embodiments have bi-layer, tri-layer, or other multi-layer configurations. Some embodiments may be continuously asymmetric with the asymmetric region extending from an upper surface of the material to a lower surface of the material. Optionally, some embodiment may have only one or more portions of the material that are asymmetric while one or more other regions are isotropic in terms of pore size. Some embodiments may have an asymmetric material that is then bonded to at least another material that is isotropic to create a desired pore size distribution profile. In such an embodiment, the asymmetric region may have the larger pore sizes and be coated with anti-hemolytic material. Some embodiments can have separation materials with gradation in coating material thickness and/or coverage to position material such as the hemolysis-preventing material in areas where the material is likely to be in contact with formed components captured by the separation material.

By way of non-limiting example, some separation materials may be washed in a manner the preferentially removes the anti-hemolytic material from at least one region of the separation material, such as the inner portions of the separation material, but not the exterior portions that are more likely to come into direct contact with formed components of the bodily fluid. Other variations or alternative coating schemes to create separation materials or filter structures with areas of leaching and non-leaching materials are not excluded. Optionally, separation materials can also be coated with at least two different materials that may both leach into the bodily fluid, but at least one of these materials that may leach into the fluid does not impact assay measurements and can be used to overcoat the other material and thus decrease the surface area exposure of the other material to the bodily fluid.

Optionally, the separation material comprises an asymmetric porous membrane. Optionally, the separation material is a mesh. Optionally, the separation material comprises polyethylene (coated by ethylene vinyl alcohol copolymer). Optionally, at least a portion of the separation material comprises a polyethersulfone. Optionally, at least a portion of the separation material comprises an asymmetric polyethersulfone. Optionally, at least a portion of the separation material comprises polyarylethersulfone. Optionally, at least a portion of the separation material comprises an asymmetric polyarylethersulfone. Optionally, at least a portion of the separation material comprises a polysulfone. Optionally, the separation material comprises an asymmetric polysulfone. Optionally, the separation material comprises a cellulose or cellulose derivative material. Optionally, the separation material comprises polypropylene (PP). Optionally, the separation material comprises polymethylmethacrylate (PMMA).

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

INCORPORATION BY REFERENCE

All publications, patents, and patent applications mentioned in this specification are herein incorporated by reference to the same extent as if each individual publication, patent, or patent application was specifically and individually indicated to be incorporated by reference. References cited herein are hereby incorporated by reference in their entirety, except to the extent that they conflict with teachings explicitly set forth in this specification.

DESCRIPTION OF THE SPECIFIC EMBODIMENTS

Figure 1:
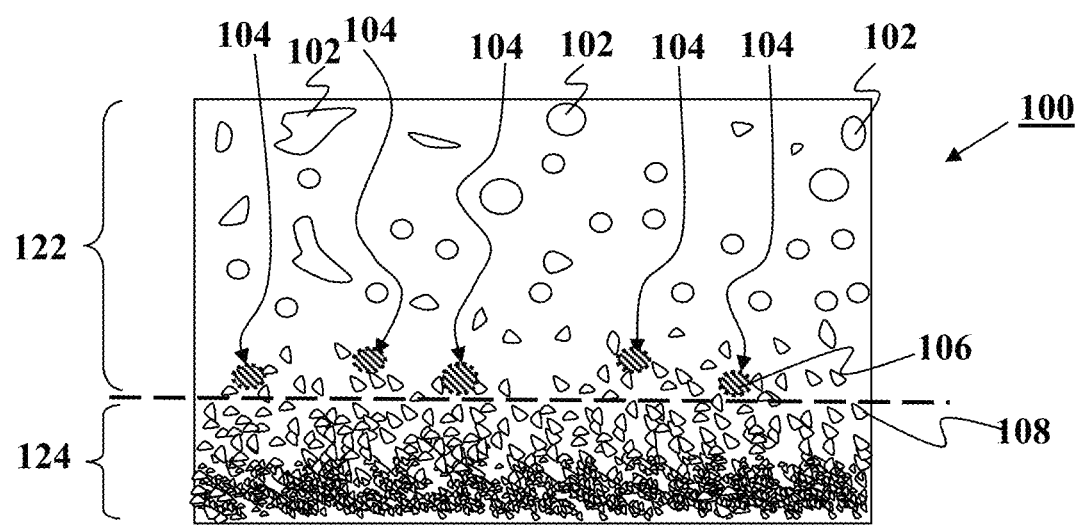
FIG. 1 shows a side, cross-sectional view of a separation material according to one embodiment described herein.

It is to be understood that both the foregoing general description and the following detailed description are exemplary and explanatory only and are not restrictive of the invention, as claimed. It may be noted that, as used in the specification and the appended claims, the singular forms "a", "an" and "the" include plural referents unless the context clearly dictates otherwise. Thus, for example, reference to "a material" may include mixtures of materials, reference to "a compound" may include multiple compounds, and the like.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for a sample collection unit, this means that the sample collection unit may or may not be present, and, thus, the description includes both structures wherein a device possesses the sample collection unit and structures wherein sample collection unit is not present.

As used herein, the terms "substantial" means more than a minimal or insignificant amount; and "substantially" means more than a minimally or insignificantly. Thus, for example, the phrase "substantially different", as used herein, denotes a sufficiently high degree of difference between two numeric values such that one of skill in the art would consider the difference between the two values to be of statistical significance within the context of the characteristic measured by said values. Thus, the difference between two values that are substantially different from each other is typically greater than about 10%, and may be greater than about 20%, preferably greater than about 30%, preferably greater than about 40%, preferably greater than about 50% as a function of the reference value or comparator value.

As used herein, a "surfactant" is a compound effective to reduce the surface tension of a liquid, such as water. A surfactant is typically an amphiphilic compound, possessing both hydrophilic and hydrophobic properties, and may be effective to aid in the solubilization of other compounds. A surfactant may be, e.g., a hydrophilic surfactant, a lipophilic surfactant, or other compound, or mixtures thereof. Some surfactants comprise salts of long-chain aliphatic bases or acids, or hydrophilic moieties such as sugars. Surfactants include anionic, cationic, zwitterionic, and non-ionic compounds (where the term "non-ionic" refers to a molecule that does not ionize in solution, i.e., is "ionically" inert). For example, surfactants useful in the reagents, assays, methods, kits, and for use in the devices and systems disclosed herein include, for example, Tergitol™ nonionic surfactants and Dowfax™ anionic surfactants (Dow Chemical Company, Midland, Mich. 48642); polysorbates (polyoxyethylenesorbitans), e.g., polysorbate 20, polysorbate 80, e.g., sold as TWEEN® surfactants (ICI Americas, New Jersey, 08807); poloxamers (e.g., ethylene oxide/propylene oxide block copolymers) such as Pluronics® compounds (BASF, Florham Park, N.J.); polyethylene glycols and derivatives thereof, including Triton™ surfactants (e.g., Triton™ X-100; Dow Chemical Company, Midland, Mich. 48642) and other polyethylene glycols, including PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, sucrose monostearate, sucrose monolaurate, sucrose monopalmitate, PEG 10-100 nonyl phenol series, PEG 15-100 octyl phenol series, and poloxamers; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; phosphocholines, such as n-dodecylphosphocholine, (DDPC); sodium dodecyl sulfate (SDS); n-lauryl sarcosine; n-dodecyl-N,N-dimethylamine-N-oxide (LADO); n-dodecyl-β-D-maltoside (DDM); decyl maltoside (DM), n-dodecyl-N,N-dimethylamine N-oxide (LADO); n-decyl-N,N-dimethylamine-N-oxide, 1,2-diheptanoyl-sn-glycero-3-phosphocholine (DHPC); 1,2-dilauroyl-sn-glycero-3-phosphocholine (DLPC); 2-methacryloyloxyethyl phosphorylcholine (MPC); 1-oleoyl-2-hydroxy-sn-glycero-3-[phospho-RAC-(1-glycerol)] (LOPC); 1-palmitoyl-2-hydroxy-sn-glycero-3-[phospho-RAC-(1-glycerol)] (LLPG); 3-[(3-cholamidopropyl) dimethylammonio]-1-propanesulfonate (CHAPS); n-Octyl-N,N-dimethyl-3-ammonio-1-propanesulfonate; n-Decyl-N,N-dimethyl-3-ammonio-1-propanesulfonate; n-Dodecyl-N,N-dimethyl-3-ammonio-1-propanesulfonate; n-Hexadecyl-N,N-dimethyl-3-ammonio-1-propanesulfonate; Tetradecanoylamidopropyl-dimethylammonio-propanesulfonate; Hexadedecanoylamidopropyl-dimethylammonio-propanesulfonate; 4-n-Octylbenzoylamido-propyl-dimethylammonio Sulfobetaine; a Poly(maleic anhydride-alt-1-tetradecene), 3-(dimethylamino)-1-propylamine derivative; a nonyl phenoxylpolyethoxylethanol (NP40) surfactant; alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins, including lecithin, lysolecithin, phosphatidylcholine, phosphatidylethanolamine, phosphatidylglycerol, phosphatidic acid, phosphatidylserine; lysolecithins and hydrogenated lysolecithins; phospholipids and derivatives thereof; lysophospholipids and derivatives thereof, including lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof; alkylmaltosides; alkylthioglucosides; lauryl macrogolglycerides; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and combinations thereof.

As used herein, the term "separator", "separation material", or "separation membrane" may include a mesh, a filter, a membrane, a porous membrane, an asymmetric porous membrane, a semipermeable hollow fiber membrane, a percolating network structure, a material that can be used for size-exclusion of objects greater than a certain dimension, or other filtering material. Materials useful for the preparation of the separator or separation material may be selected from the group comprising polyethylene (coated by ethylene vinyl alcohol copolymer), polyacrylates, polystyrene, polyethylene oxide, cellulose, cellulose derivatives, polyethersulfone (PES), polypropylene (PP), polysulfone (PSU), palymethylmethacrylate (PMMA), polycarbonate (PC), polyacrylonitrile (PAN), polyamide (PA), polytetrafluorethylene (PTFE), cellulose acetate (CA), regenerated cellulose, and blends or copolymers of the foregoing, or blends or copolymers with hydrophilizing polymers, including with polyvinylpyrollidone (PVP) or polyethyleneoxide (PEO). Suppliers of such materials and/or membranes include but are not limited to BASF, Advanced Microdevices P. Ltd., International Point of Care Inc., Gambro Lundia AB, Asahi Kasei Kuraray Medical Co., Ltd., GE Healthcare (Whatman division), or the like.

Referring now to FIG. 1, one embodiment of a filtering device such as but not limited to a bodily fluid separation material 100 will now be described. FIG. 1 shows a side cross-sectional view of the separation material 100, showing cross-sections of the structures 102 of the separation material. By way of non-limiting example, the separation material 100 may be a size-exclusion barrier such as but not limited to a porous membrane with size-exclusion properties. Other embodiments may use other types of size-exclusion barrier(s). In one embodiment described herein, the structures 102 are fibers in the separation material with their cross-sectional views shown in FIG. 1. Optionally, the structures 102 are mesh portions of the separation material. Optionally, the structures 102 are pore walls or pore-defining structures of the separation material. Optionally, the structures 102 may be a percolating network of connected fibers, elongate members, or the like. Some embodiments may combine one or more of the foregoing to form the separation material. Although the descriptions herein are written in the context of a separation material, other filter materials or structures in sheet-like or other shapes are not excluded material. FIG. 1 shows that for the present embodiment, formed components 106 such as but not limited to red blood cells, white blood cells, platelet, or other formed components of the bodily fluid can enter the separation material 100 in a variety of directions, including from a top-down manner, and will continue to pass through the separation material until the component reaches a size-constrained area where the spacing becomes too small for the formed component 106 to proceed any further. In this embodiment, operating under the principle of size exclusion, the formed component 106 will then be constrained in the separation material 100 while liquid portions and/or those components not size excluded can continue to pass through the separation material. In one non-limiting example, arrows 104 show movement of formed components through the separation material 100 of FIG. 1. Other movement, such as but not limited to lateral, side-ways, and/or diagonal movement, is not excluded.

Referring still to the embodiment of FIG. 1, the dotted line 120 shows that in this embodiment, there are at least two regions 122 and 124 for the separation material 100. It should be understood that other embodiments can have even more regions. In this current embodiment, the region 122 comprises a formed component capture region. In some specific embodiments as will be discussed in more detail below, it may be an anti-hemolytic, formed component capture region. By way non-limiting example, the region 124 comprises a pass-through region that has structural elements spaced closely enough that formed components of the bodily fluid sample cannot completely pass through that region 124. In at least some embodiments, the sizing and/or spacing of elements is selected such that the size-restriction technique of separation material components prevents the formed components from continuing through the separation material. This filters out the formed components from the liquid components of the bodily fluid.

In one embodiment, because region 122 can be configured to be a formed component capture region, structures in the region 122 will have more potential direct contact with the formed components 106 and be in contact with them for a longer period of time, relative to structures in the second region 124. Due at least in part to the greater direct contact physically and temporally, it may be desirable in it at least some embodiments described herein to treat the structures 102 of the region 122 to minimize undesirable breakdown, spoilage, or other detrimental effect that may result from the formed components being captured in the region 122. In one non-limiting example, the structures 102 may be coated with an anti-hemolytic coating to prevent breakdown of red blood cell when the bodily fluid being processed is blood. One embodiment of an anti-hemolytic coating may be an NTA coating. Optionally, other anti-hemolytic treatments in layer or other form may use material such as but not limited to n-Octyl-β-D-Glucopyranoside (OG), cell lipid bilayer intercalating material, phosphate ester containing at least two ester linkages comprising fatty hydrocarbon groups, tri-2-ethylhexylphosphate, di-2-ethylhexylphthalate, dioctyl-terephthalate, anti-hemolytic surfactant(s), a surfactant such as but not limited to polysorbate 80 mixed with any of the foregoing, and/or other anti-hemolytic material. Other anti-hemolytic material used with embodiments herein includes but is not limited to one or more of the following: anti-coagulants, proteins (such as but not limited to BSA, HSA, Heparin, Casein, etc.), surfactants (such as but not limited to Tween, Silwet, SDS, etc.), sugars (such as but not limited to sucrose, trealose, etc.), and/or the like.

In one embodiment, the region 124 may be configured to be a liquid pass-through region positioned after the bodily fluid has passed through region 122. Although FIG. 1 illustrates region 124 to be next to region 122, it should be understood that embodiments having intermediate region(s) and/or space between the regions are not excluded. By way of non-limiting example, the pass-through region 124 may be configured not have direct contact with the formed components. Optionally, only structures 108 defining part of the upper portion of the region 124 may be in contact with any formed components 106. Optionally, only structures 108 defining part of the upper surface of the region 124 may be in contact with any formed components 106. In one embodiment, the region 124 may be have a selected structure size, spacing, and/or other property that prevents formed components 106 from passing through the region 124 so as to enable a size restriction filtering technique for removing formed components from the bodily sample.

In at least some embodiments, because the formed components are not in direct contact with the region 124 or are only in minimal contact with region 124, the separation material of region 124 may not be coated with the material used in the region 122. Optionally, region 124 may be selective coated with the materials used in region 122 in a manner such as but not limited to only those portions that might still be in contact with formed components may be coated, which others portions of region 122 are uncoated. Optionally, at least some embodiments may have some or all of region 124 coated with a material different from that of the region 122. Optionally, at least some embodiments may have some or all of region 124 covered with the material of region 122 and then adding a second layer of the second material over the material of region 122. In one non-limiting example, this second material may be selected to prevent the first material leaching or otherwise entering the bodily fluid when the liquid passes through the region 124. In at least some embodiments, the portions of region 124 covered with the material of region 122 is covered with the second material while other areas of region 124 are substantially or at least partially uncovered by either material. By way of example and not limitation, some embodiments may use Heparin and/or other anti-coagulant as the material for the second layer. Optionally, the material for the second layer may be a material that is already in the bodily fluid sample. By way of non-limiting example, the material may be EDTA if the bodily fluid sample has already been or will be treated with EDTA. Optionally, for the second layer, some embodiments may use inert materials alone or in combination with any of the other materials listed herein.

Figure 2:
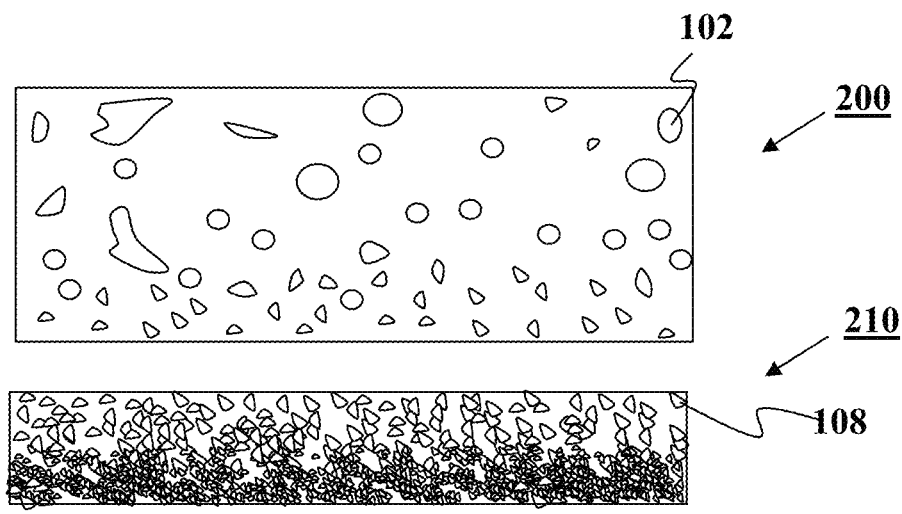
FIG. 2 shows an exploded side, cross-sectional view of separation materials according to one embodiment described herein.

Referring now to FIG. 2, a still further embodiment will now be described. This embodiment shows a first separation material 200 and a second separation material 210. Although only two separation materials are shown, it should be understood that other embodiments having additional separation materials above, between, and/or below the separation materials shown in FIG. 2 are not excluded. It should also be understood that one or more of the separation materials 200 and 210 can, within the separation materials themselves, each have additional regions therein for different properties.

As seen in the embodiment of FIG. 2, the separation material 200 functions as a capture region similar to the capture region 122 of the embodiment of FIG. 1. In the current embodiment, the separation material 210 functions as a pass-through region similar to region 124 of the embodiment of FIG. 1.

Figure 3:
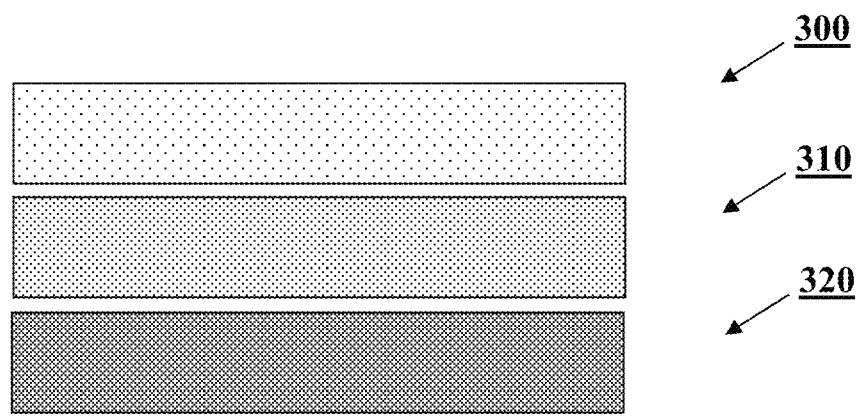
FIG. 3 is schematic of a multi-layer separation material according to one embodiment described herein.

Referring now to FIG. 3, this embodiment shows a tri-layer filter assembly with a first layer 300, a second layer 310, and a third layer 320. For ease of illustration, the layers are shown to be similar in thickness, but configurations where all three are of different thicknesses, or only are of different thicknesses are not excluded. Embodiments with additional layers are also not excluded. Layers can also be formed of different materials.

It should be understood that any of the layers 300, 310, or 320 can be configured as a capture region, a pass-through region, or neither. In one non-limiting example, at least the upper two layers 300 and 310 are capture regions. They can have similar capture capabilities, or optionally, one can be configured to be preferential capture of components while the other layer has preferential capture of components in a different size and/or shape regime. In another non-limiting example, at least the upper two layers 300 and 310 are captures regions, but only one of them is coated with a material to prevent degradation of the formed component(s). Optionally, both of them are coated with a material to prevent degradation of the formed component(s). Another embodiment may have two layers such as layers 310 and 320 that are both configured as pass-through layers. In one embodiment, neither of the layers 310 or 320 have structures that are coated with a material to prevent degradation of the formed component(s). Optionally, at least one of the layers 310 or 320 has structures that are coated with a material to prevent degradation of the formed component(s). Optionally, some embodiments have both of the layers 310 or 320 have structures that are coated with a material to prevent degradation of the formed component(s).

Separation Material Treatment

By way of example and not limitation, in order to be able to use separation materials for producing plasma suitable for a greater range of assays, several separation material treatment methods have been identified. Some of these techniques may involve treatment of separation materials after they are formed. Some of the techniques may involve forming the separation materials in a way that does not involve additional treatment after separation material formation. Optionally, some techniques may use both separation material formation and post-formation treatment to create a desired configuration.

Figure 4:
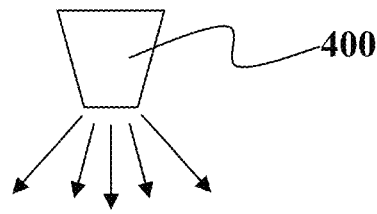
FIGS. 4 and 5 illustrate methods according to embodiments described herein.
Figure 4:
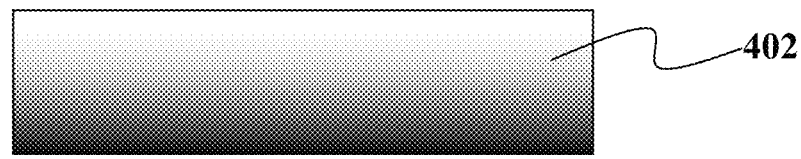

1. Separation material wash: In one embodiment described herein, by controlled washing of the coated plasma separation material by water and/or buffer solutions, most of the hemolysis-preventing agents can be removed. FIG. 4 shows that a washing mechanism, such as but not limited to a nozzle 400 directing washing fluid (as indicated by the arrows) towards the target separation material 402, can be used to reduce at least some of the coating off of the separation material. This can create a preferential change in the amount of coating in selected areas of the separation material. One example may show removal or at least reduction of coating on one side of the separation material. Optionally, some may direct the wash fluid to wash coating off of an interior region of the separation material. Other configurations where portions of coating are removed from other select areas are not excluded.

Figure 5:
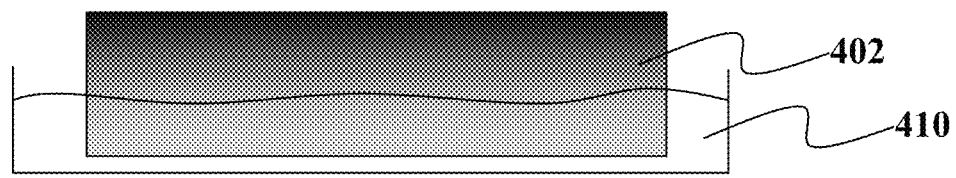

In one embodiment described herein, a carefully controlled washing is desirable so as to not completely remove the hemolysis preventing agent—which would result in hemolysis. In contrast, insufficient wash will result in sufficient amount of the hemolysis preventing agent leaching into the plasma and causing hemolysis. Thus, in one non-limiting example, a reduced amount of coating, or coating in interior portions of the separation material can be acceptable. Optionally, as seen in FIG. 5, some embodiments may also use a bath 410 of wash fluid that preferentially removes coating material from certain areas of the separation material. Optionally, spray washing and bath soaking, or vice versa, may be combined for use on a separation material. This processing may occur sequentially or simultaneously.

2. Custom separation material coating: In another embodiment described herein, both coated and uncoated versions of the plasma separation material can be coated using a custom formulation which is compatible with assay chemistries. The coating may contain one or more of the following: proteins, surfactants, sugars, organic and inorganic salts, anti-coagulants, etc. In one non-limiting example, the coating could be applied to an initially uncoated separation material to prevent hemolysis. Optionally, an initially coated separation material may be further coated to prevent assay interfering substances from leaching into the bodily fluid from the separation material.

3. Charge Neutralization: In one embodiment described herein, separation material surface charge can be neutralized to prevent retention of small, oppositely charged ions. For example, the separation material with NTA coating has a negatively-charged surface, which can be neutralized to prevent retention of positively charged $Ca^{++}$ ions. Optionally, if a coating has a positively-charged surface and is in turn attracting negatively charged ions in a detrimental manner, the member will be treated to neutralize the undesired charge condition.

4. Other techniques and/or materials may also be used to create a filter such as a separation material that has anti-hemolytic qualities on the capture surfaces of the filter and non-leaching qualities on other surfaces of the filter. Some embodiments may combine one or more of the foregoing techniques on a separation material. By way of non-limiting example, one embodiment may have coated and uncoated regions on a separation material along with having been treated to achieve charge neutralization before, during, and/or after coating.

EXAMPLES

Using a dynamic wash technique, asymmetric membranes were washed with high performance liquid chromatography (HPLC) grade water and then tested. In one non-limiting example, the membrane has a pore volume of 2 μL per 10 $mm^2$ of membrane. The pore loading is defined as the ratio of the total volume of blood to the pore volume. For a blood volume of 40 μL with membrane surface area of 100 $mm^2$, this corresponds to a pore loading of 2×. The wash procedure comprised pre-mounting membrane in a fixture for filtration. In this particular example, about 600 uL of water is directed through the membrane and then the water is discarded. This wash process of directing water through the membrane was repeated, which in this particular example, involved repeating the wash five (5) times. After washing, the membranes are allowed to dry. Filtration of the dynamically washed membranes were then tested.

Washing by way of soaking ("static wash") rather than the flow-through technique ("dynamic wash") can create differences in the performance of the resulting membrane. In at least some static washed membranes, anti-hemolytic is preferentially removed from the large pore region. In at least some dynamic wash membranes, anti-hemolytic is preferentially removed from the small pore region. This asymmetry in coating material may be desirable when the formed blood components contact the membrane where the pores are larger while only plasma contacts the smallest pores. Hemolysis prevention happens only in the regions where RBCs can enter or be contacted (i.e. the large pore region). It is not possible to hemolyze plasma and thus coating the small pore region with anti-hemolytic does not result in noticeable performance benefit. As noted herein, the excess anti-hemolytic may have adverse impact on assay results for the assays sensitive to excess anti-hemolytic coating.

In static wash, diffusion dominates removal of anti-hemolytic. In some embodiments of the membrane, large pores may be ~50× bigger than small pores. Mass diffusion rate is proportional to cross sectional flow area. Thus diffusion rate of anti-hemolytic away from membrane on large pore side may be ~2500× greater than on small pore side. Thus, without being bound to any particular theory, total removal should be much greater on large pore side, where the RBCs contact the membrane.

In dynamic wash, shear dominates removal of anti-hemolytic. Shear increases dramatically with decreasing diameter. Without being bound to any particular theory, total removal should be greater in small pore regions, where shear is most significant.

In yet another embodiment, the coating on the membrane can be a material that provides a negative charge. Without being bound to any particular theory, a negative charge repels formed blood component that have a negative polarity, and thereby reduces mechanical trauma inflicted on such formed blood components via contact with the membrane during filtration. Some embodiments may use formulations with negatively charged substances to coat all or optionally selective areas on the membrane. One embodiment may use casein 0.5%, Tween 20 1.35%, sucrose 5%, 15 minute soak time. Optionally, one embodiment may use Li-Heparin 50 mg/mL, sucrose 5%. Optionally, one embodiment may use Li-Heparin 50 mg/mL, Tween 80 1.35%, sucrose 5%. Optionally, one embodiment may use Casein 1.0%, Tween 20 2.70%, sucrose 5%. Optionally, one embodiment may use Li-Heparin 100 mg/mL, Tween 20 2.70%, sucrose 5%.

While the teachings has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, with any of the above embodiments, it should be understood that the fluid sample may be whole blood, diluted blood, interstitial fluid, sample collected directly from the patient, sample that is on a surface, sample after some pre-treatment, or the like. Although the embodiments herein are described in the context of an anti-hemolytic coating, it should be understood that these embodiments may also be configured for use with other types of coatings, including but not limited to other coatings which may undesirably mix into the bodily fluid upon prolonged fluid exposure. Other material used with embodiments herein may include but is not limited to one or more of the following: anti-coagulants, proteins (BSA, HSA, Heparin, Casein, etc.), surfactants (Tween, Silwet, SDS, etc.), sugars (sucrose, trealose, etc.)

Although the embodiments herein are described in the context of capturing formed components such as blood cells or platelets, it should be understood that these embodiments can also be adapted for use with fluid containing other solid, semi-solid, or formed components or particles. Although the embodiments herein are described in the context of separation material, it should be understood that these embodiments can also be adapted for use other filter materials such as meshes, porous layers, or other layer like materials or structures.

Additionally, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a size range of about 1 nm to about 200 nm should be interpreted to include not only the explicitly recited limits of about 1 nm and about 200 nm, but also to include individual sizes such as 2 nm, 3 nm, 4 nm, and sub-ranges such as 10 nm to 50 nm, 20 nm to 100 nm, etc. . . . . .

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference to disclose and describe the structures and/or methods in connection with which the publications are cited. The following applications are fully incorporated herein by reference for all purposes:

OTHER EMBODIMENTS

In one embodiment described herein, a bodily fluid separation material is provided comprising a formed component capture region and a bodily fluid pass-through region. The pass-through region has structures with a reduced liquid leaching quality relative to than the capture region, wherein during separation material use, bodily fluid enters the capture region prior to entering the pass-through region. Optionally, a bodily fluid pass-through region has a reduced amount of liquid leaching material relative to than the capture region.

In another embodiment described herein, a bodily fluid separation material is provided comprising an anti-hemolytic and formed component capture region; and a bodily fluid pass-through region having less anti-hemolytic material than the capture region, wherein during separation material use, bodily fluid enters the capture region prior to entering the pass-through region.

In yet embodiment described herein, a bodily fluid separation material is provided comprising a first filter region of the separation material having an anti-hemolytic coating and mesh spacing sized to constrain formed blood components therein; a second filter region of the separation material having mesh spacing smaller than mesh spacing of the first filter region and configured to have an amount of anti-hemolytic coating less than that of the first region.

In a still further embodiment described herein, a bodily fluid separation material is provided comprising a percolating network of structures wherein a first region of the percolating network with an anti-hemolytic coating on structures in the region, said structures sized and spaced to allow formed blood components to enter the first region but constraining blood components therein from passing completely through the first region; and a second region of the percolating network with a reduced anti-hemolytic coating on structures sized and spaced to prevent formed blood components from entering the second region, wherein bodily fluid passes through the first region prior to reaching the second region.

It should be understood that embodiments herein may be adapted to include one or more of the following features. For example, the separation material may be an asymmetric separation material. Optionally, the anti-hemolytic material on the separation material comprises single and/or double alkyl chain N-oxides of tertiary amines (NTA). Optionally, the first region comprises a first separation material layer and the second region comprises a second separation material layer. Optionally, the separation material comprises a first separation material coupled to a second separation material. Optionally, the separation material comprises at least two separate separation materials. Optionally, there may be at least another region of the separation material between the first region and the second region. Optionally, the first region of the separation material may be in fluid communication with the second region. Optionally, the first region may be spaced apart from the second region.

In yet another embodiment described herein, a method is provided for forming a bodily fluid separation material. The method comprises coating the separation material with an anti-hemolytic coating on a first region and a second region of the separation material; reducing anti-hemolytic effect of the second region of the separation material relative to the first region, wherein when the separation material is in operation, bodily fluid passes through the first region prior to reaching the second region.

It should be understood that embodiments herein may be adapted to include one or more of the following features. For example, the method may include reducing the anti-hemolytic effect by washing off at least a portion of the anti-hemolytic coating on the second region. Optionally, washing off comprises directing solvent through the separation material. Optionally, washing off comprises soaking only a portion of the separation material in a solvent. Optionally, reducing the anti-hemolytic effect comprises adding another coating of a different material over the anti-hemolytic coating on the second region. Optionally, reducing the anti-hemolytic effect comprises treating the separation material to bring its electrical charge state to a neutral state and thus reduce the attraction of ions that increase the anti-hemolytic effect.

In yet another embodiment described herein, a method is provided for forming a bodily fluid separation material. The method comprises coating at least a first region of the separation material with an anti-hemolytic coating; not coating at least second region of the separation material with the anti-hemolytic coating. Optionally, some embodiments have a bilayer structure based on a substantially even coating of anti-hemolytic material, but instead has a region of substantially greater pore size than another region. Although the material may be asymmetric, it is a not a linear gradient, but instead has a rapid change in pore size at an inflection point when pore size is graphed in depth from top of the layer to bottom of the layer.

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference to disclose and describe the structures and/or methods in connection with which the publications are cited. The following applications are fully incorporated herein by reference for all purposes: U.S. Pat. Nos. 8,088,593; 8,380,541; U.S. patent application Ser. No. 13/769,798, filed Feb. 18, 2013; U.S. patent application Ser. No. 13/769,779, filed Feb. 18, 2013; U.S. Pat. App. Ser. No. 61/766,113 filed Feb. 18, 2013, U.S. patent application Ser. No. 13/244,947 filed Sep. 26, 2011; PCT/US2012/57155, filed Sep. 25, 2012; U.S. application Ser. No. 13/244,946, filed Sep. 26, 2011; U.S. patent application Ser. No. 13/244,949, filed Sep. 26, 2011; and U.S. Application Ser. No. 61/673,245, filed Sep. 26, 2011, U.S. Patent Application Ser. No. 61/786,351 filed Mar. 15, 2013, U.S. Patent Application Ser. No. 61/697,797 filed Sep. 6, 2012, U.S. Patent Application Ser. No. 61/799,221 filed Mar. 15, 2013, and U.S. Patent Application Ser. No. 61/733,886 filed Dec. 5, 2012, the disclosures of which patents and patent applications are all hereby incorporated by reference in their entireties for all purposes.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Any feature, whether preferred or not, may be combined with any other feature, whether preferred or not. The appended claims are not to be interpreted as including means-plus-function limitations, unless such a limitation is explicitly recited in a given claim using the phrase "means for." It should be understood that as used in the description herein and throughout the claims that follow, the meaning of "a," "an," and "the" includes plural reference unless the context clearly dictates otherwise. For example, a reference to "an assay" may refer to a single assay or multiple assays. Also, as used in the description herein and throughout the claims that follow, the meaning of "in" includes "in" and "on" unless the context clearly dictates otherwise. Finally, as used in the description herein and throughout the claims that follow, the meaning of "or" includes both the conjunctive and disjunctive unless the context expressly dictates otherwise. Thus, the term "or" includes "and/or" unless the context expressly dictates otherwise.

What is claimed is:

1. A filter device comprising:
   a bodily fluid separation material comprising a first capture region formed of a first material and having an anti-hemolytic surface coating not comprising the first material;
   a second capture region formed of the first material and without the anti-hemolytic surface coating not comprising the first material;
   a bodily fluid pass-through region formed of the first material and comprising pass-through openings sized so that formed components of the bodily fluid do not enter the bodily fluid pass-through region.

2. The device of claim 1 wherein at least a portion of the separation material comprises an asymmetric polyethersulfone.

3. The device of claim 1 wherein at least a portion of the separation material comprises polyarylethersulfone.

4. The device of claim 1 wherein at least a portion of the separation material comprises an asymmetric polyarylethersulfone.

5. The device of claim 1 wherein at least a portion of the separation material comprises a polysulfone.

6. The device of claim 1 wherein the separation material comprises an asymmetric polysulfone.

7. The device of claim 1 wherein the anti-hemolytic surface coating comprises single and/or double alkyl chain N-oxides of tertiary amines (NTA).

8. The device of claim 1 wherein the first capture region defines a first filter region of the separation material having an anti-hemolytic coating and pore spacing sized to constrain formed blood components therein;
   wherein the bodily fluid pass-through region defines a second filter region of the separation material having pore spacing smaller than pore spacing of the first filter region with pores sized so that formed components do not enter the second filter region and configured to have an amount of anti-hemolytic coating less than that of the first region.

9. The device of claim 8 wherein the separation material comprises at least two separate separation materials.

10. The device of claim 8 further comprising at least another region of the separation material between the first region and the second region.

11. The device of claim 8 where the first region is in fluid communication with the second region.

12. The device of claim 8 wherein the first region is spaced apart from the second region.

13. The device of claim 1 wherein the first capture region, second capture region, and the bodily fluid pass-through region comprise a percolating network.

14. The device of claim 1 wherein the separation material has a flat, planar shape.

15. A kit comprising the device of claim 1 wherein at least a portion of the separation material comprises a polyethersulfone.

* * * * *